United States Patent [19]

Finney

[11] Patent Number: 4,622,958
[45] Date of Patent: Nov. 18, 1986

[54] PENILE IMPLANT WITH ACCUMULATOR
[75] Inventor: Roy P. Finney, Spring Hill, Fla.
[73] Assignee: Medical Engineering Corporation, Racine, Wis.
[21] Appl. No.: 680,746
[22] Filed: Dec. 12, 1984
[51] Int. Cl.[4] .............................................. A61F 5/00
[52] U.S. Cl. ..................................................... 128/79
[58] Field of Search ........................................ 128/79

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,201,202 | 5/1980 | Finney et al. | 128/79 |
| 4,267,829 | 5/1981 | Burton et al. | 128/79 |
| 4,318,396 | 3/1982 | Finney | 128/79 |
| 4,342,308 | 8/1982 | Trick | 128/79 |
| 4,353,360 | 10/1982 | Finney et al. | 128/79 |
| 4,360,010 | 11/1982 | Finney | 128/79 |
| 4,364,379 | 12/1982 | Finney | 128/79 |
| 4,383,525 | 5/1983 | Scott et al. | 128/79 |
| 4,399,811 | 8/1983 | Finney et al. | 128/79 |
| 4,399,812 | 8/1983 | Whitehead | 128/79 |
| 4,407,278 | 10/1983 | Burton et al. | 128/79 |

FOREIGN PATENT DOCUMENTS

WO80/00302 3/1980 PCT Int'l Appl. .

Primary Examiner—Robert P. Swiatek
Assistant Examiner—Cary E. Stone
Attorney, Agent, or Firm—Quarles & Brady

[57] ABSTRACT

An inflatable penile implant includes a novel pressure accumulating chamber which has a wall which stretches to expand the volume of the chamber when the normal working pressure of the implant has been exceeded. The expansion in the volume of the chamber absorbs and compensates for any increased pressure and thereby protects the components of the hydraulic system from pressure damage.

2 Claims, 9 Drawing Figures

PENILE IMPLANT WITH ACCUMULATOR

TECHNICAL FIELD

The present invention relates to inflatable implants. More particularly, it relates to a inflatable penile implant which includes a novel pressure accumulator which absorbs sharp increases in pressure and protects the components of the implant from pressure damage.

BACKGROUND OF THE INVENTION

Inflatable penile implants depend upon closed hydraulic systems to maintain a desired pressure in a pressure chamber for extended periods of time. In U.S. Pat. No. 4,353,360, an inflatable penile implant is described which includes a pressure chamber which is a non-distensible cylindrical chamber. When the pressure chamber is pressurized, it becomes rigid and the penis assumes an erectile state.

The components of the hydraulic system of inflatable penile implants are made of the suitable materials and are designed to operate reliably under conditions which normally might be encountered. There are, however, occasions in which the pressure within the pressure chamber may greatly exceed that for which the components were designed. For example, when the implant and its inflated pressure chamber are accidentally bent or squeezed, a much higher pressure than normal can be generated within the hydraulic system. Such increased pressures can cause damage to the hydraulic system components and cause the implant to fail.

There is a need for an effective means of absorbing and compensating for accidental sharp increases in pressure which could damage the components of an inflatable penile implant.

SUMMARY OF THE INVENTION

It is the primary object of the present invention to disclose an implant which includes an effective means for absorbing and compensating for pressure peaks which might otherwise damage the hydraulic systems of the penile implants.

The inflatable penile implant of the present invention includes a novel pressure accumulator means which absorbs sharp increases in pressure and protects the components of the implant from pressure damage. The pressure accumulator means is a chamber which expands in volume only when the normal working pressure of the implant has been exceeded. The chamber preferably has an elastomeric wall that stretches when normal working pressures are exceeded thereby increasing the volume of the chamber. The expansion in volume of the chamber absorbs and compensates for the increased pressure. The chamber may be at the tip or stem, in the pumping chamber, or even in the pressure chamber itself.

In the preferred embodiment, the penile implant is of the double cylinder type described in U.S. Pat. No. 4,353,360 and the pressure accumulating means is a chamber adjacent the stem which has an elastomeric wall which expands only when the normal working pressure of the implant is exceeded.

Further objects and advantages to the invention will become apparent to those skilled in the art from the description of the preferred embodiment and the drawings.

BEST MODE OF CARRYING OUT THE INVENTION

Figure 1:
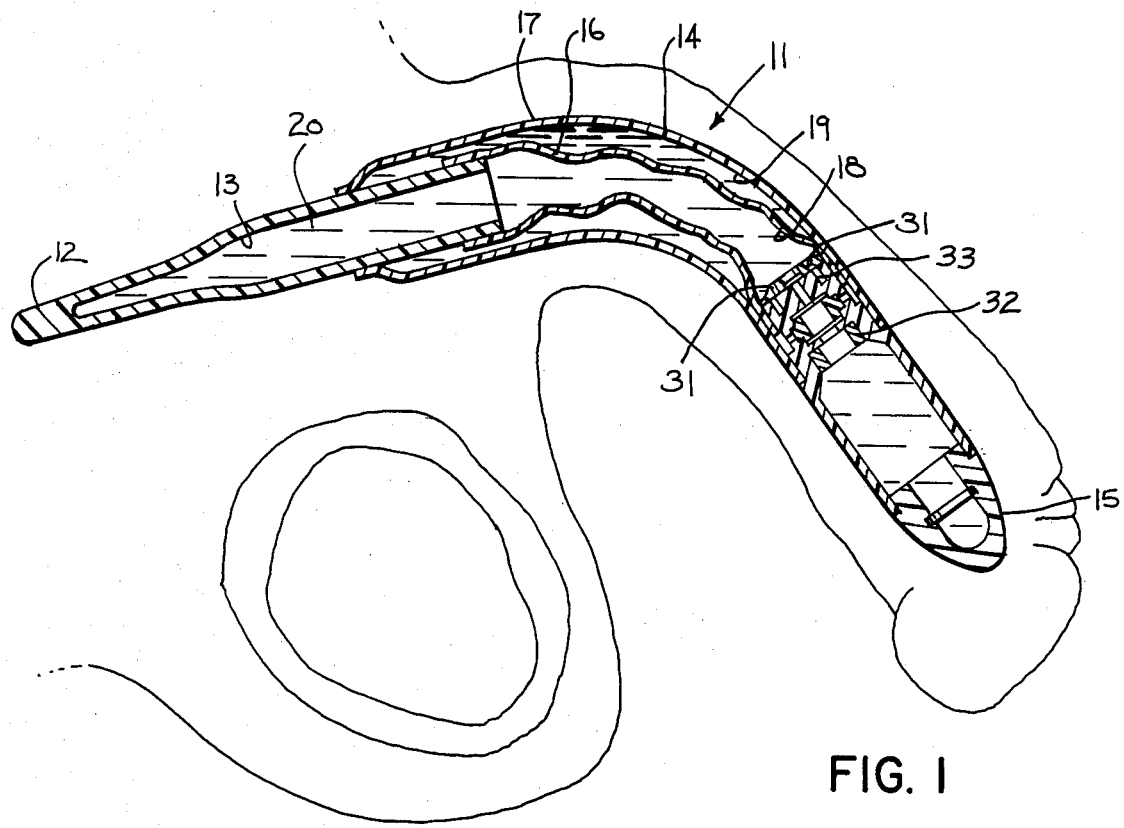
FIG. 1 is a side view, partly in section, of a penile erectile system including a preferred embodiment of the penile implant of the present invention with a pressure accumulating chamber near the stem. One of the two identical penile implants is shown surgically implanted in a male and in a non-pressurized condition.
Figure 2:
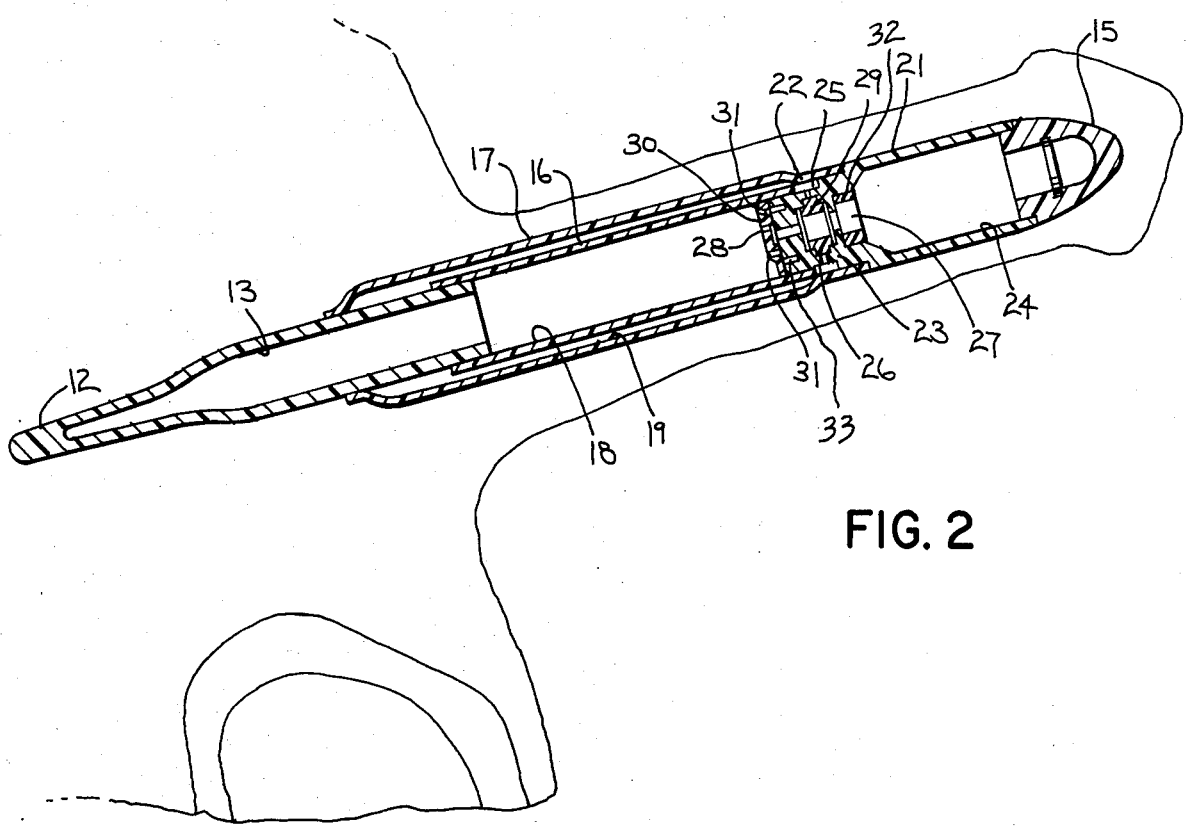
FIG. 2 is a side view similar to FIG. 1, except that the implant is pressurized.
Figure 3:
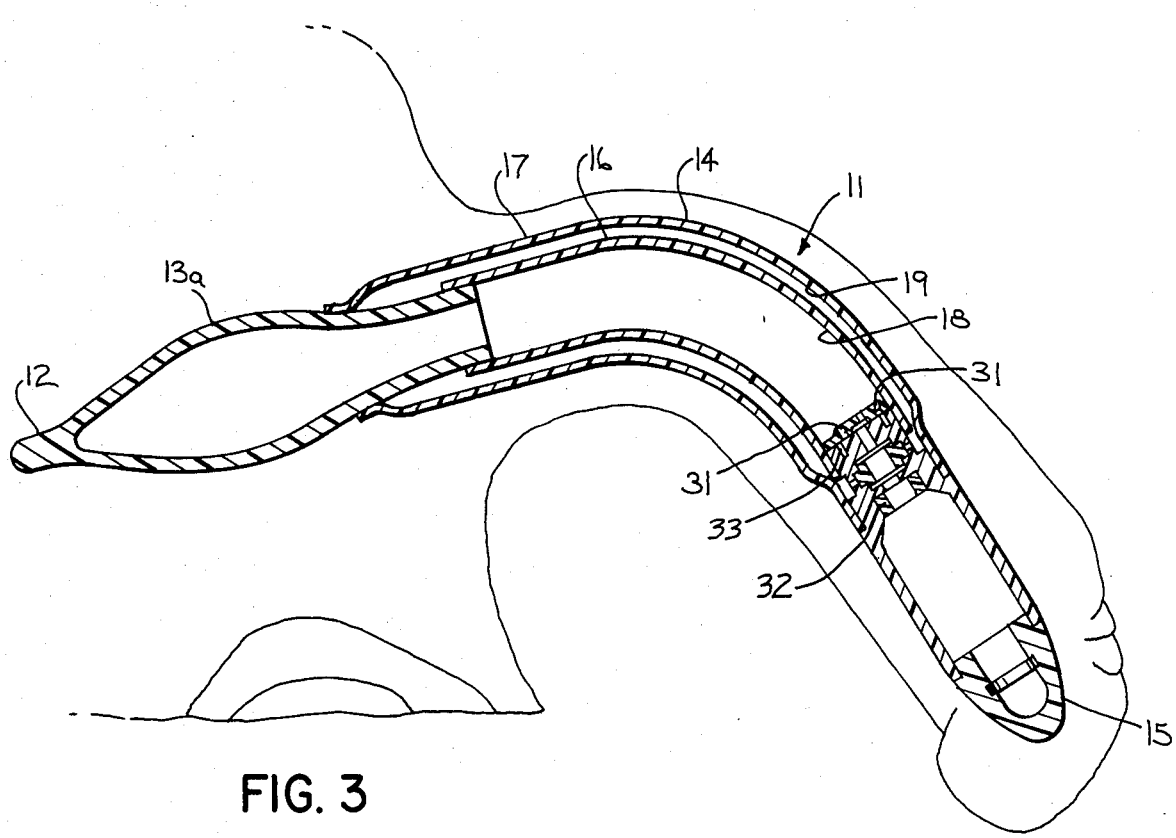
FIG. 3 is a side view similar to FIG. 2, except that the implant is subjected to higher than normal pressures.

The preferred penile erectile system, which is shown in FIGS. 1-3, is of the type disclosed in U.S. Pat. No. 4,399,811. It comprises a pair of penile implants which are to be implanted in the corpora cavernosa of the penis. The two implants are identical, therefore, only one will be described in detail.

As seen in FIGS. 1 to 3 of the drawings, the implant 11 has a short, proximal stem 12, an accumulating chamber 13, an intermediate cylindrical portion 14, and a conical distal tip 15. The stem 12 which is of a relatively stiff material is implanted in the root end of a corpus cavernosum the accumulating chamber 13 is implanted in the crus and the flexible cylindrical portion 14 and the tip 15 are implanted in the portion of the corpus cavernosum in the pendulous penis. Each of the two implants is positioned in a separate corpus cavernosum of the penis.

The intermediate cylindrical portion 14 of the implant 11 includes a pair of concentric cylindrical sleeves 16 and 17 which are attached in a fluid tight manner to the outer wall of the accumulating chamber 13 and to the tip 15 to form a pair of concentric chambers 18 and 19, respectively. The sleeve 16 which forms the wall of the inner chamber 18 is of an inelastic material so that the chamber 18 is nondistensible even when pressurized. The sleeve 16 also cooperates with the sleeve 17 which is spaced outwardly from the sleeve 16 to form the outer chamber 19. The sleeve 17 may be made of a distensible material such as nonreinforced silicone rubber. The necessary fluid tight seals between the sleeves 16 and 17 and the stem 12 and tip 15 may be made with a silicone adhesive or by other suitable means.

As seen in FIG. 1, when the implant 11 is in a non-pressurized state both the chambers 18 and 19 are substantially filled with a non-compressible hydraulic fluid 20 which may be a biocompatible fluid such as saline or a free flowing silicone gel. In the non-pressurized state, the soft, flexible, intermediate cylindrical portion 14 of the implant 11 flexes and permits the penis to assume a substantially normal, flaccid position as seen in FIG. 1. However, when the implant 11 is in the pressurized state as seen in FIG. 2, the intermediate cylindrical portion 14 is rigid as the result of the non-distensible inner chamber 18 becoming a pressure chamber completely filled with fluid under pressure. The penis then assumes an erectile position.

The integral pump 21 and release valve 22 for pressurizing the inner chamber 18 and relieving the fluid pressure in the chamber 18, respectively, will now be described in connection with FIG. 2.

As seen in FIG. 2, a valve housing 23 separates the chambers 18 and 19 from a pumping chamber 24 adjacent the tip 15. An inlet passage 25 in the housing 23 leads from the outer chamber 19 to the pumping chamber 24. An inlet valve 26 controls the flow of fluid 20 from chamber 19 to pumping chamber 24. An outlet passage 27 in the housing 23 leads from the pumping chamber 24 to the pressure chamber 18. The exit of the passage 27 which leads to the chamber 18 is normally closed by an outlet valve 28.

When the pumping chamber 24 is squeezed the passage 25 is closed by the inlet valve 26 which consists of a deformable ring 29 which flattens and seats against an annular groove in the housing 23. When the fluid pressure in the outer chamber reservoir 19 exceeds that in the pumping chamber 24 the ring 29 is pulled off its seat permitting fluid to enter the pumping chamber 24.

The outlet valve 28 includes a diaphragm 30 which closes the exit of the passage 27. The diaphragm 30 forms a seal about the exit of passage 27 when the pressure in the pressure chamber 18 exceeds that in the pumping chamber 24. When the resilient wall of the pumping chamber 24 is squeezed the fluid pressure in the pumping chamber 24 exceeds that in pressure chamber 18 and the diaphragm 30 is moved out of sealing engagement with the housing 23 allowing fluid to flow from the pumping chamber and passage 27 through openings 31 in the diaphragm 30. Although only two openings 31 are shown, the diaphragm 30 will usually have four or more such openings.

The implant 11 is pressurized by sequentially squeezing the pumping chamber 24 to force the fluid 20 from the pumping chamber 24 into nondistensible pressure chamber 18 under pressure. When the pumping chamber is first squeezed the fluid 20 originally in the pumping chamber 24 is forced through the passage 27 into the pressure chamber 18. The increased pressure in the pumping chamber 24 flattens the deformable ring 29 against its seat closing passage 25 and preventing fluid from flowing into reservoir chamber 19.

When the squeezing force is removed, a reduced pressure is formed in the pumping chamber 24 and as a result the ring 29 is sucked off its seat allowing fluid 20 to flow from chamber 19 into the pumping chamber 24.

When the pressure chamber 18 is sufficiently pressurized and rigid, the pumping action is stopped whereby the exit of the passage 27 is closed by pressure of the fluid 20 in pressure chamber 18 upon the backside of the diaphragm 30 which causes the ring seal of the diaphragm 29 to seat as seen in FIGS. 1, 2 and 3.

The pressure chamber 18 can be depressurized by manually squeezing and deforming the housing 23 so that leak paths exist about the inlet valve 26 and outlet valve 28. The deformation of the housing 23 causes the diaphragm 30 to bow away from sealing engagement with the housing 23 so that a first leak path exists whereby fluid 20 can leave the pressure chamber 18. The deformation also causes the ring 29 to be moved off its seat so that a second leak path exists so that the fluid from the pressure chamber 18 can return to the reservoir 19. There is a stiffening ring 32 which prevents the housing 23 from being deformed during pumping and an annular groove 33 in the housing 23 about the exit of passage 27 which makes it easier to deform the housing 23 to establish the leak paths.

The non-distensible inner chamber 18 of the penile implants must when pressurized provide rigidity sufficient to maintain the penis in an erectile position. Therefore, it must be of sufficient volume and size to perform this function either alone or in combination with another implant. In contrast, the outer chamber 19 serves primarily as a reservoir of pressurizing fluid for the inner chamber and is sized accordingly. The exact dimensions of the inner and outer chambers are not critical as long as they are adequate to provide their desired function.

In the preferred embodiment of the penile implant of the present invention seen in FIGS. 1 to 3, the accumulating chamber 13 is adjacent the stem 12. As can be seen in FIG. 3, when the pressurized implant 10 is bent or otherwise subjected to increased external pressure, the wall 13a of the chamber 13 expands outwardly under the force of the increased pressure in the hydraulic system of the implant. The wall 13 is constructed of an elastomeric material which does not stretch until an internal pressure exceeding the normal working pressure of 900 cm of $H_2O$ is exceeded. When the pressure drops to 900 cm of $H_2O$ or below the wall 13a resumes its original non-stretched condition.

The elasticity of the wall 13a can be controlled in any number of acceptable ways. The wall may be made of a more elastomeric material than the rest of the implant or it may be made thinner, so that it will expand more easily when the working pressure is exceeded. To prevent over-stretching of the wall, the elastomeric material of the wall may also be reinforced with crimped threads which limit the expansion as described in U.S. Pat. No. 4,201,202.

In FIGS. 4 to 9, several other embodiments of implants having pressure accumulating chambers are shown.

Figure 4:
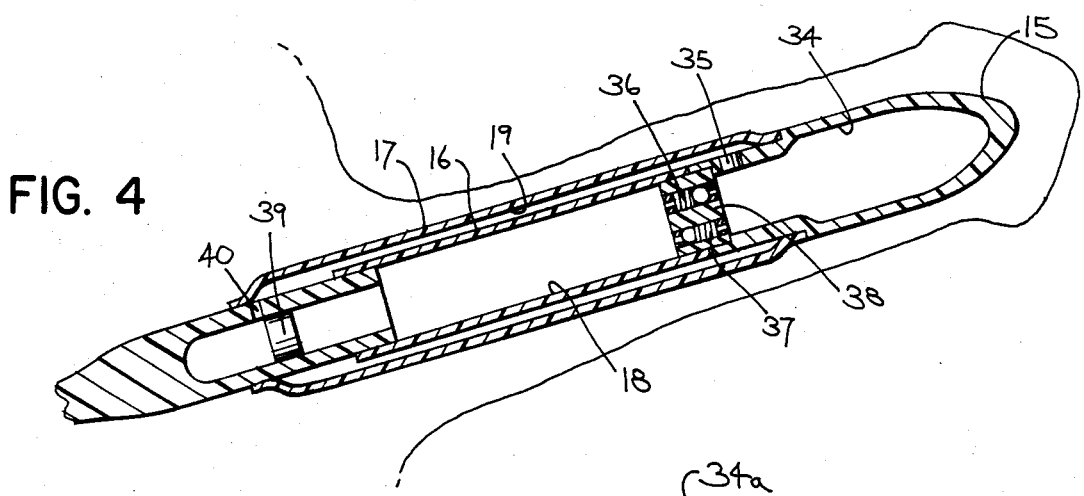
FIG. 4 is an enlarged view, partially in section, of the distal tip portion of an implant in which the accumulating chamber is in the tip and showing the condition of the tip when the implant is at working pressure.
Figure 5:
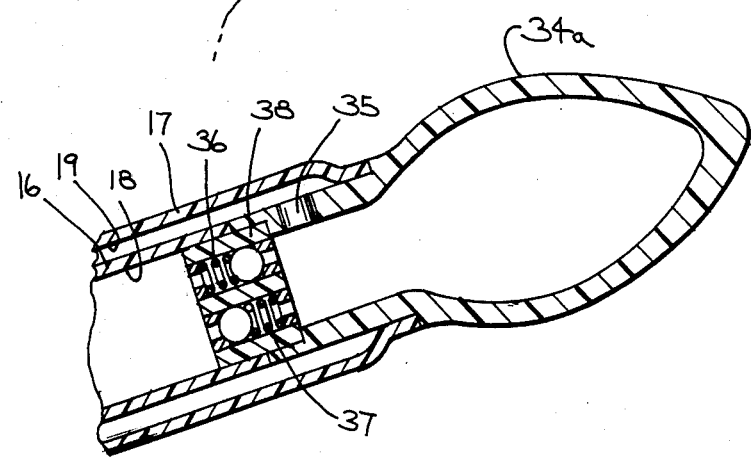
FIG. 5 is a view similar to FIG. 4, showing the condition of the tip when the implant is subjected to greater than normal pressures.

In the implant of FIGS. 4 and 5, the accumulating chamber is the pumping chamber 34 adjacent the tip 15. An inlet valve 35 is located between pumping chamber 34 and the reservoir chamber 19 and an outlet valve 36 and a relief valve 37 are located in a wall 38 separating the pumping chamber 34 and the pressure chamber 18. The outlet valve 36 opens when the pressure in the pumping chamber 34 exceeds that in the pressure chamber 18 and the relief valve 37 opens when the pressure chamber 18 exceeds 900 cm of $H_2O$. The pumping chamber 34 has an elastomeric wall 34a which stretches when subjected to higher than working pressures as seen in FIG. 5. A manually operable valve 39 controls flow from the pressure chamber 18 to a port 40 which leads to the reservoir chamber 19.

Figure 6:
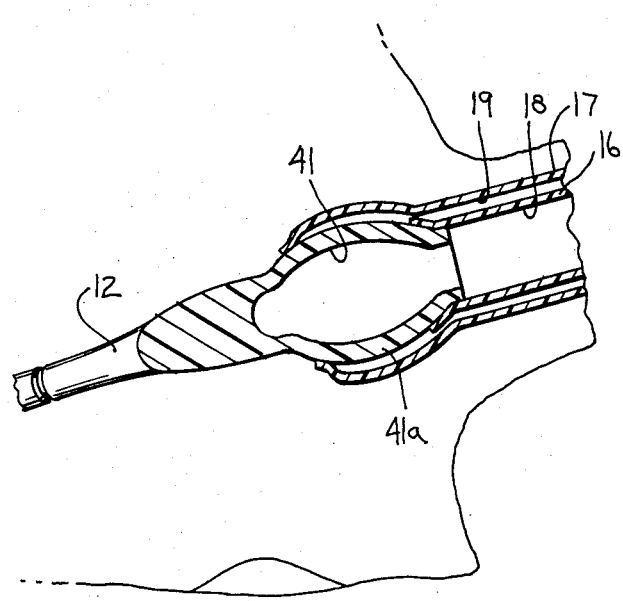
FIG. 6 is an enlarged view, partly in section, of the proximal stem portion of another embodiment of an implant in which the accumulating chamber is subjected to greater than normal pressure.

In the embodiment of FIG. 6 the accumulating chamber is a reservoir chamber 41 located adjacent the stem 12. The chamber 41 has an elastomeric wall 41a which expands as seen when greater than working pressures are created. The embodiment of FIG. 6 has a pump and a squeeze to please valve (not shown) at the tip end.

Figure 7:
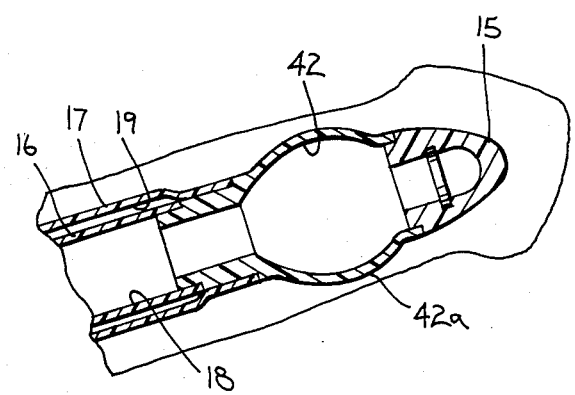
FIG. 7 is an enlarged view, partly in section, of another embodiment of an implant in which the accumulating chamber is subjected to greater than normal pressure.

In the embodiment of FIG. 7 an accumulating chamber 42 is adjacent the hollow tip 15 and the pump and relief valve (not shown) are at the stem end. The chamber 42 has an elastomeric wall 42a which expands as seen when greater than working pressure is encountered.

Figure 8:
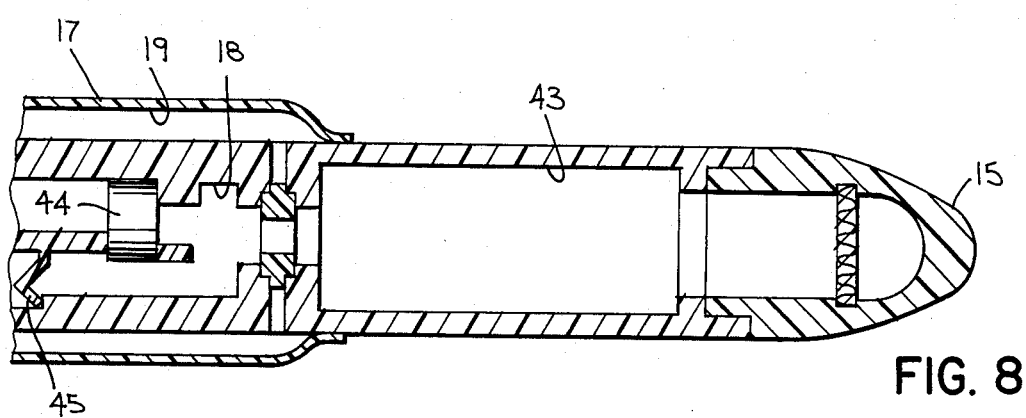
FIG. 8 is an enlarged view, partly in section, of the distal tip portion of an implant having a combination pump and accumulator chamber showing the implant at working pressure.
Figure 9:
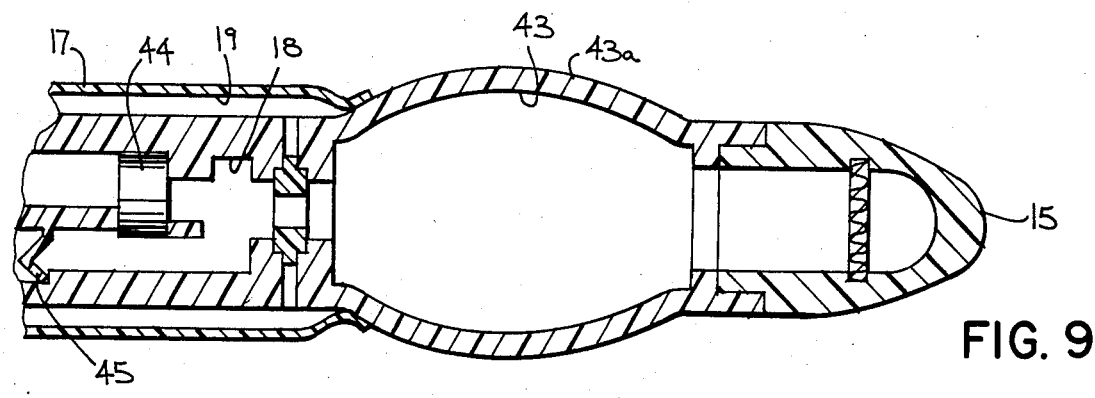
FIG. 9 is an enlarged view of the implant of FIG. 8 showing the accumulating chamber subjected to greater than normal pressure.

The penile implant, shown in part, in FIGS. 8 and 9 has a combined pump and accumulating chamber 43. When a higher than normal working pressure is created in the pressure or inner chamber 18 a relief valve 44 opens and permits fluid to flow back into the pump and accumulating chamber 43. If the pressure in the chamber 43 is great enough the chamber wall 43a swells as is seen in FIG. 9. A normally closed outlet valve 45 prevents the fluid from leaving the pressure chamber 18 when the fluid pressure in the chamber is at or below the normal working pressure.

All the components of the described implants are preferably made of biocompatible materials having the necessary properties to function as intended.

The sleeve 16 which forms the wall of the "non-distensible" pressure chamber 18 must be relatively inelastic and is preferably made of a dacron mesh or fabric covered with silicone material that will not stretch when filled with fluid and pressurized. When the pressure chamber 18 is the accumulating chamber, the sleeve 16 which serves as the elastomeric wall can be made of an elastomeric material reinforced with crimped threads which will expand only a predetermined amount as described in U.S. Pat. No. 4,201,202.

The sleeve 17 may be distensible or non-distensible. It is preferably less distensible than the wall of the accumulating chamber. The diameters of the sleeves 16 and 17 can vary but are normally sized so that the implant in the non-pressurized state will fill the corpus cavernosum. It will be appreciated that the terms distensible, non-distensible and inelastic an intended to cover any materials which possess the desired properties which enable them to provide the described functions.

The proximal stem 12 of tne implant preferably has a Shore A hardness of about 70, the distal tip 15 has a Shore A hardness of about 20, and each of the materials has sufficient tensile strength for its intended use.

The term "substantially filled" as used herein to describe the fluid content of a chamber in the penile implant means that a chamber contains about 60% to about 95% or more of its capacity of a non-compressible fluid such as water, saline or a free flowing gel. The actual content of fluid can vary; however, the implant when "substantially filled" should be still sufficiently flexible so that the penis can assume a normal flaccid position.

All the parts and components of the prosthesis are preferably made of or covered with medical grade silicone rubber which is non-reactive, non-toxic and well tolerated by the adjacent organic tissues. Silicone rubber is preferred because it is quite resistant to wear and remains functional for long periods of time. However, other suitable materials possessing desirable properties may also be employed.

The preferred method of implantation of the erectile system of FIGS. 1 to 3 is through an incision made in the penis. After appropriate incision, each corpus cavernosum is dilated distally and proximally to accept the implants. The appropriate anatomical measurements are made to insure that the proximal end of the implant or implants will be positioned is the proximal crus. Preferably, the pump is located in the distal corpra near the glans but it can be also located at the penile base partly under the pubic bone. An implant or implants having an appropriately sized intermediate section and distal tip is inserted into the corpus cavernosum of the penis. The distal tip is positioned in the glans end of the corpus cavernosum. The stem at the proximal end of the implant then is anchored in the root end of the corpus cavernosum.

The identical procedure is performed on the other side of the penis to complete the surgical procedure. The stems of the two implants preferably will diverge laterally to accommodate the anatomy, to provide lateral stability to the penis and to help prevent rotation of the implants. The incision is then closed.

It will be understood that the foregoing description has been for purposes of illustration and that the accumulating means of the present invention may be used with other designs of inflatable implants than that described. Therefore, the invention is not to be limited except by the claims which follow.

I claim:

1. In an inflatable penile implant comprising a generally cylindrical body containing a hydraulic system which includes a non-distensible pressure chamber, a reservoir and a pump for transferring pressurizing fluid from the reservoir to the pressure chamber, the improvement which comprises said non-distensible pressure chamber having a minor portion thereof a wall which expands outwardly of said pressure chamber to increase the volume of the pressure chamber when the normal working pressure of the hydraulic system of the implant has been exceeded thereby absorbing and compensting for any increased pressures which might otherwise damage the hydraulic system.

2. An inflatable penile implant of claim 1 in which the wall portion is of an elastomeric material.

* * * * *